United States Patent [19]

Nakashima et al.

[11] Patent Number: 4,833,267

[45] Date of Patent: May 23, 1989

[54] METHOD FOR PRODUCTION OF UNSATURATED CARBOXYLIC ACID ESTERS

[75] Inventors: Sumio Nakashima; Hideki Sogabe, both of Himeji; Hiroshi Yoshida, Toyonaka; Atsushi Okubo, Kawanishi, all of Japan

[73] Assignee: Nippon Shokubai Kagaku Kogyo Co., Ltd., Osaka, Japan

[21] Appl. No.: 193,523

[22] PCT Filed: Jul. 7, 1987

[86] PCT No.: PCT/JP87/00482

§ 371 Date: Mar. 9, 1988

§ 102(e) Date: Mar. 9, 1988

[87] PCT Pub. No.: WO88/00180

PCT Pub. Date: Jan. 14, 1988

[30] Foreign Application Priority Data

Jul. 9, 1986 [JP]  Japan .................................. 61-159674

[51] Int. Cl.[4] ............................................. C07C 69/52
[52] U.S. Cl. ..................................................... 60/205

[58] Field of Search ......................................... 560/205

[56] References Cited

U.S. PATENT DOCUMENTS

| 3,037,052 | 5/1962 | Bortnick | 560/205 |
| 3,470,238 | 9/1969 | Asano et al. | 560/205 |
| 3,882,167 | 5/1975 | Lohmar | 560/205 |
| 4,733,004 | 3/1988 | Pascol | 560/205 |

*Primary Examiner*—Paul J. Killos
*Attorney, Agent, or Firm*—Burns, Doane, Swecker & Mathis

[57] ABSTRACT

This invention relates to a method for the production of unsaturated carboxylic acid esters. More particularly, this invention relates to a method for efficient production of a corresponding ester from an acrylic acid or methacrylic acid (hereinafter referred to collectively as "(meth)acrylic acid") by the reaction of the (meth)acrylic acid with an aliphatic alcohol of 1 to 12 carbon atoms in the presence of a strongly acidic cation-exchange resin catalyst.

12 Claims, 1 Drawing Sheet

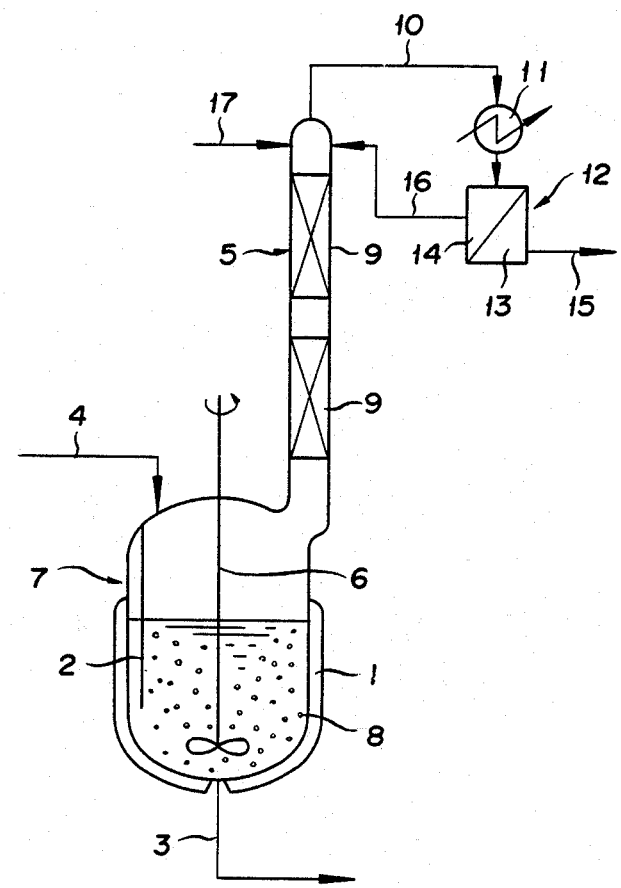

METHOD FOR PRODUCTION OF UNSATURATED CARBOXYLIC ACID ESTERS

BACKGROUND ART

In a method which produces a corresponding ester from a (meth)acrylic acid by the reaction of the acid with an aliphatic alcohol of 1 to 12 carbon atoms, the esterification proceeds in the form of an equilibrious reaction. When a lower aliphatic alcohol of 1 to 3 carbon atoms is selected as an alcohol source, therefore, the reaction is continuously carried out by using a reactor having a strongly acidic cation-exchange resin packed as a catalyst in the form of a fixed bed therein and the resultant reaction product which is equilibrated in composition is distilled to effect separation of the ester and the formed water from the reaction product. The unaltered (meth)acrylic acid is recovered from the residue for reuse. When a higher aliphatic alcohol of 4 to 12 carbon atoms is selected, there is generally adopted a process which uses sulfuric acid, phosphoric acid, benzenesulfonic acid, or other similar acid as a catalyst, promotes the reaction by expelling the formed water from the reaction system with a solvent such as benzene, toluene, or xylene, deprives the reaction product of acid components through neutralization and washing with water, and finally refines the reaction product.

Recently, use of a strongly acidic cation-exchange resin is recommended even when the esterification is carried out with a higher aliphatic alcohol of 4 to 10 carbon atoms. For example, Japanese Patent Laid-Open SHO 51(1976)-65,712 and Japanese Patent Laid-Open SHO 53(1978)-56,611 disclose a method for esterifying acrylic acid with n-butanol in a reaction column having a strongly acidic cation-exchange resin packed in the form of a fixed bed therein. Japanese Patent Publication SHO 46(1971)-3,041 discloses a method which, in a reactor having a strongly acidic cation-exchange resin as a catalyst for esterification packed in the form of a fixed bed therein and connected to the liquid inlet part and the liquid outlet part of a plate tower, carried out the esterification of acrylic acid with butanol under a vacuum, distils the water formed by the reaction through the top of the tower, and separates the butanol and the ester entrained by the formed water.

None of these methods, however, proves to be satisfactory for the purpose of carrying out the esterification on a commercial scale because in the production of an ester, the selectivity of the reaction for the ester is not sufficiently high. To be specific, these methods are found to suffer from the following disadvantages. In the first place, when the reaction is continuously carried out in a reactor which has a strongly acidic cation-exchange resin packed as a catalyst in the form of a fixed bed, persistence of the water formed by the reaction in the reaction system poses a problem. Since the esterification proceeds in an equilibrious state, presence of water in a liquid state within the reaction system inevitably represses the ratio of conversion. The persisting water further enhances the occurrence of secondary products such as dimeric acids and esters thereof, hydroxypropionic acid and esters thereof and consequently degrades the selectivity of the reaction for the corresponding ester. In the second place, in the esterification using a higher alcohol of 4 to 12 carbon atoms as a raw material, the reaction is promoted by using sulfuric acid, phosphoric acid, benzenesulfonic acid, or other similar acid as a catalyst and causing the formed water to be removed from the reaction system with a solvent such as benzene, toluene, or xylene. During the removal of the formed water, the (meth)acrylic acid is liable to be entrained by the removed water. Effective recovery of the entrained (meth)acrylic acid from the distillate is obtained only with difficulty. Virtually always, the entrained (meth)acrylic acid is inevitably discarded. Even during the course of neutralization and washing with water which follows the course of reaction, the ester produced readily undergoes hydrolysis inevitably to lower the yield of the ester aimed at.

A method which uses a strongly acidic cation-exchange resin as a catalyst and causes this catalyst to be fluidized within the reaction solution has been known to the art. To be specific, Japanese Patent Laid-Open SHO 49(1974)-54,326 discloses a method which comprises introducing an inert gas upwardly into a reaction zone from the lower part thereof, causing the suspension of a catalyst in the reaction solution to be fluidized from the lower part to the upper part of the reaction zone, allowing the suspension to be circulated within a return conduit, and returning it to the lower part of the reaction zone. Since this method effects the fluidization of the catalyst by introducing the inert gas into the reaction zone, it requires introduction of a large amount of the inert gas. Paticularly when the reaction is carried out under a vacuum, this method necessitates incorporation of a voluminous device as for vacuumization in the production system and, therefore, proves to be disadvantageous from the economic point of view.

An object of this invention, therefore, is to provide a method for producing a corresponding ester in a high yield from a corresponding (meth)acrylic acid by the reaction of the acid with an aliphatic alcohol of 1 to 12 carbon atoms.

Another object of this invention is to provide a method for producing a corresponding ester in a high yield from a (meth)acrylic acid by the reaction of the acid with a higher aliphatic alcohol of 4 to 12 carbon atoms.

DISCLOSURE OF THE INVENTION

The objects described above are accomplished by a method for the production of a corresponding ester from the acrylic acid or methacrylic acid by the reaction of the acid with an aliphatic alcohol of 1 to 12 carbon atoms in the presence of a strongly acidic cation-exchange resin as a catalyst, which method is characterized by retaining the reaction solution in a boiling state and carrying out the reaction while keeping the catalyst suspended and dispersed in the reaction solution by means of a stirrer possessed of a motive force in the range of 0.005 to 2 kW per m$^3$ of the reaction solution.

The aforementioned objects are further accomplished by a method for the production of a corresponding ester from the acrylic acid or methacrylic acid by the reaction of the acid with an aliphatic alcohol of 4 to 12 carbon atoms in the presence of a strongly acidic cation-exchange resin as a catalyst, which method is characterized by retaining the reaction solution in a boiling state and carrying out the reaction solution by means of a stirrer possessed of a motive force in the range of 0.005 to 2 kW per m$^3$ of the reaction solution, and refluxing the alcohol as the raw material into contact with the vapor composed chiefly of the water formed by the esterification and expeled by distillation from the esterification system thereby separating and recovering from the distilled water the acrylic acid or methacrylic acid entrained by the formed water.

This invention has originated in a new knowledge that in the esterification of (meth)acrylic acid with an aliphatic alcohol of 1 to 12 carbon atoms in the presence of a strongly acidic cation-exchange resin as a catalyst, when the strongly acidic cation-exchange resin as the catalyst is used as packed in the form of a fixed bed within the reactor, water stagnates for a long time within the catalyst bed and hinders the progress of the esterification and that efficient fluidization of the catalyst within the reaction system forms an effective measure to prevent of the esterification from the aforementioned hindrance. This knowledge coupled with the effort continued in search of a method for boiling and, at the same time, forcibly stirring the reaction system has resulted in perfection of the present invention.

BRIEF DESCRIPTION OF THE DRAWING

Drawing is a schematic diagram illustrating a typical reactor to be used in working the method of the present invention.

BEST MODE FOR CARRYING OUT THE INVENTION

Now, the present invention will be described in detail below with reference to the accompanying drawing.

As illustrated in drawing, in a reactor 7 which is provided on the with exterior thereof with a jacket 1 for heating, on the interior thereof with one baffle 2, on the bottom thereof with a reaction solution discharge pipe 3, in the upper part thereof with a raw material feeding pipe 4 and a distillation tower 5, and on the inside thereof with a stirrer 6, strongly acidic cation-exchange resin 8 is placed and a raw material solution composed of (meth)acrylic acid and an alcohol is fed in through the raw material feeding pipe 4. After the reactor 7 has thus been charged to a prescribed amount, the stirrer 6 is set rotating to stir the contents and fluidize the ion-exchange resin and the heating jacket 1 is operated to keep the raw material solution in a boiling state. The vapor generated in the reactor 7 and containing the water formed by the esterification, unaltered alcohol, and the produced ester is allowed to rise inside the distillation tower 5 filled with a packing 9 or a distillation tower 5 of some other form such as a plate tower or a bubble tower, depart from the top of the tower, and flow through a line 10 to a condenser 11. The condensate formed in the condenser 11 is forwarded to a separator 12. A water layer 13 separated in the separator 12 is discharged as the formed water through a line 15, whereas an organic layer 14 is refluxed via a line 16 to the distillation tower 5. When the alcohol as the raw material is supplied via the line 16 to the top of the distillation tower 5, the (meth)acrylic acid existing inside the distillation tower 5 is absorbed by the alcohol. The distillate from the top of the distillation tower, therefore, does not substantially contain (meth)acrylic acid. As the result, the water layer obtained after the condensation and separation does not substantially contain (meth)acrylic acid and can be discharged safely into the sewer without requiring any special treatment. Further, since the (meth)acrylic acid is collected by the alcohol and returned to the reactor 5, the loss of this acid is virtually nil.

As concerns the type of the blade for the stirrer to be used for this invention, any of the conventional blades in popular use such as turbine blades, fan turbine blades (paddle blades), inclined-vane fan turbine blades, and Faudler blades can be used. A desired combination of these plades can also be used. For the purpose of minimizing the possible disintegration of the catalyst beads by the impact of stirring, adoption of the Faudler blades proves to be particularly desirable.

For the purpose of keeping the reaction solution in a boiling state and effecting fluidization of the catalyst as contemplated by the present invention, the motive force required for the stirrer is in the range of 0.005 to 2 kW per $m^3$ of the reaction solution, preferably in the range of 0.01 to 1 kW per $m^3$ of the reaction solution. If the motive force mentioned above is less than 0.005 kW per $m^3$ of the reaction solution, the catalyst is not fluidized sufficiently in the reaction solution and the reaction velocity is lowered and the conversion is degraded even when the reaction solution is kept in a boiling state. Conversely, if the motive force exceeds 2 kW, the disintegration of the strongly acidic cation-exchange resin beads by friction occurs heavily and the ratio of recovery of the catalyst from the reaction system is lowered and the ratio of conversion is degraded.

The catalyst to be used in the present invention is a strongly acidic cation-exchange resin in the form of beads 0.1 to 2.0 mm in diameter. This strongly acidic cation-exchange resin is desired to have a small specific surface area and a small porosity. Particularly desirably, the strongly acidic cation-exchange resin has a particle diameter in the range of 0.1 to 2.0 mm, a cross-linking degree in the range of 2 to 20%, a specific surface area in the range of 0.1 to 5 $m^2/g$, and a porosity of not more than 10% by volume. For example, commercially available grades of the strongly acidic cation-exchange resin include Amberlite IR-116 and Amberlite IR-120B (both produced by Rohm and Haas Company) as Diaion PK-208 and Diaion PK-228 (both produced by Mitsubishi Chemical Industries, Ltd.).

Of course, the reaction can be carried out batchwise or continuously.

The ratio (in mol) of the amount of (meth)acrylic acid to that of an aliphatic alcohol of 1 to 12 carbon atoms is in the range of 1:0.5 to 1:3, preferably 1:0.7 to 1:2. If the amount of the alcohol to be used is unduly large, the ratio of conversion of (meth)acrylic acid to be used is unduly large, the ratio of conversion of (meth)acrylic acid is enhanced but the recovery of excess alcohol calls for a large cost. Conversely, it the amount of (meth)acrylic acid to be used is unduly large, the ratio of conversion is heightened but the cost for recovery of (meth)acrylic acid is high. Thus, the ratio of the amounts of (meth)acrylic acid and alcohol is desired to be approximated to 1:1 as much as possible.

Generally, the reaction is carried out at a temperature in the range of 50° to 150° C., preferably 70° to 120° C., under a pressure in the range of 20 to 760 mmHg, preferably 50 to 400 mmHg (absolute). These conditions can be suitably selected for the purpose of keeping the reaction solution in a boiling state, depending on the molar ratio of (meth)acrylic acid to alcohol, the reaction temperature, and the kind of alcohol to be used.

The reaction solution and the catalyst are in the state of a slurry. The slurry concentration is desired to fall in the range of 10 to 60% by volume, preferably 30 to 50% by volume. If the slurry concentration is less than 10% by volume, the concentration of the catalyst is so small as to lower to ratios of conversion of (meth)acrylic acid and alcohol. Conversely if the slurry concentration exceeds 60% by volume, the friction between the catalyst beads is intensified to the extent of inducing loss of the catalyst by disintegration.

In the present invention, for the purpose of preventing the reaction solution from undergoig polymerization, any of the conventional polymerization inhibitors in popular use such as hydroquinone, hydroquinone monomethyl ether, and phenothiazine can be used in an amount of 0.001 to 0.5% by weight, preferably 0.01 to 0.2% by weight, based on the amount of (meth)acrylic acid.

In accordance with this invention, the retention of the reaction solution in the boiling state is attained by heating the reaction solution under reflux. The reflux of the reaction solution is generally carried out with the aforementioned distillation tower. As regards the type of the distillation tower, any of the conventional towers for distillation such as packed tower, plate tower, bubble tower, and other similar towers can be used. In this distillation tower, the water formed by the esterification reaction and the unaltered (meth)acrylic acid are separated from each other by the action of rectification, the formed water to be discharged through the top of the tower and the (meth)acrylic acid refluxed to the distillation tower.

In the method which comprises refluxing the alcohol as a raw material into contact with the vapor composed mainly of the water formed by the reaction of esterification thereby causing the (meth)acrylic acid entrained by the formed water to be expelled from the formed water by distillation, and recovering the separated (meth)acrylic acid, though the alcohol is defined to be an aliphatic alcohol of 4 to 12 carbon atoms, it is desired by reason of the boiling point to be a higher aliphatic alcohol of 5 to 12 carbon atoms. Heretofore, in the expulsion of water by distillation from the esterification system, since the expelled water is liable to entrain the formed ester, the unaltered alcohol, and even the (meth)acrylic acid and the (meth)acrylic acid passes into the water layer, the water in the state as obtained cannot be recycled in its unmodified form and must be discarded as waste water. The condensate obtained in consequence of the condensation of the top distillate of the distillation tower separates into the organic layer composed of the produced ester and the unaltered alcohol and the water layer. Since the (meth)acrylic acid is soluble in water, it passes into the water layer. When this organic layer is refluxed to the distillation tower, therefore, the (meth)acrylic acid cannot be refluxed and is wasted. The meth under discussion, consequently, requires an expense for the disposal of waste water.

In accordance with the present invention, the (meth)acrylic acid which is distilled as entrained by the formed water can be efficiently and easily recovered and put to reuse effectively. Specifically, the (meth)acrylic acid, alcohol, and ester which are distilled simultaneously with the formed water are efficiently extracted from the efficient and recovered into the alcohol side by being brought into counterflow contact with the alcohol supplied as a raw material and then are circulated into the esterification system. The formed water condensed and separated consequently contains substantially no (meth)acrylic acid and can be substantially completely separated and recovered. Even if this formed water is directly discarded in its untreated form, therefore, the loss of (meth)acrylic acid, if any, is extremely small.

In the recovery of the available components, particularly the (meth)acrylic acid, by the alcohol, the amount of this alcohol to be used as refluxed for the purpose of the counterflow contact is desired to be not less than 10% by weight, preferably 30 to 80% by weight, based on the amount of the alcohol which is supplied for the reaction of esterification. If the amount of the alcohol for the counterflow contact is smaller than the lower limit just mentioned, there is the possibility that thorough recovery of (meth)acrylic acid will not be obtained.

Now, present invention will be described more specifically below with reference to working examples. This invention is not limited to these working examples. Wherever percents (%) are mentioned therein, they are meant as percents (%) by weight unless otherwise specifies.

EXAMPLE 1

A reaction was carried out by the use of a reactor of stainless steel 100 liters in inner volume which, as illustrated in drawing, was provided on the outside side thereof with a heating jacket, on the inner side thereof with one baffle, in the bottom part thereof with a reaction solution discharge pipe, and in the upper part thereof with a raw material feeding pipe, a distillation tower 100 mm in inside diameter, and a Faudler type stirrer adapted to permit variation of revolution number as desired. The ratio of the diameter of the blades of the stirrer to the inside diameter of the reactor which was 500 mm was 0.7. The distillation tower was packed with metal gauze made of stainless steel as packings. The reaction solution discharge tube in the bottom part was fitted with a metal gauze of 80 mesh.

The reactor was first charged with 14 liters (on dry basis) of a strongly acidic cation-exchange resin (produced by Mitsubishi Chemical Industries, Ltd. and marketed under trademark designation of "Diaion PK-208) and then supplied with a mixed solution comprising 31.4% of acrylic acid, 59.4% of 2-ethylhexanol, 9.1% of 2-ethylhexyl acrylate, and 0.1% of water until the total amount of the contents reached 50 liters. The revolution number of the stirrer was adjusted so that the motive force of stirring would reach 0.05 kW per $m^3$ of the reaction solution and the amount of steam supplied to the heating jacket of the reactor was adjusted so that the temperature of the reaction solution would reach 85° C. and the pressure within the reactor was adjusted to 70 mmHg (absolute). Through the raw material feeding pipe, a mixed solution comprising 31.4% of acrylic acid, 59.4% of 2-ethylhexanol, 9.1% of 2-ethylhexyl acrylate, and 0.1% of water was supplied at a rate of 36.7 kg per hour. To prevent polymerization in the distillation tower and the reactor, phenothiazine was fed into the distillation tower via the tower top at a rate of 0.05% based on the amount of acrylic acid supplied. The reaction solution was partly withdrawn through the bottom of the reactor to keep the amount of the contents of the reactor at the fixed level of 50 liters. The reaction was continued until the interior of the system was stabilized.

While the interior of the system was in the stable state, the organic phase was distilled out through the top of the distillation tower at a rate of 0.38 kg per hour and the water phase at a rate of 2.05 kg per hour and the reaction solution was withdrawn through the bottom of the reactor at a rate of 34.27 kg per hour. The reaction solution thus withdrawn through the bottom of the reactor contained 12.34% of acrylic acid, 27.02% of 2-ethylhexanol, 59.99% of 2-ethylhexyl acrylate, 0.16% of water, 0.06% of dimeric acid, 0.13% of 2-ethylhexyl ester of dimer acid, and 0.03% of 2-ethylhexyl hydroxypropionate. The organic phase distilled through the top of the distillation tower contained 29.7% of acrylic acid, 7.89% of iso-octene, 6.44% of water, and the balance of 2-ethylhexanol and the water phase contained 19.2% of acrylic acid and 0.31% of 2-ethylhexanol. These results of reaction indicate that the conversion of acrylic acid was 58.9% and that of 2-ethylhexanol was 56.6% and the selectivity of 2-ethylhexyl acrylate was 99.19 mol% based on acrylic acid and 98.82 mol% based on 2-ethylhexanol. The amount of the acrylic acid distilled out through the top of the distillation tower was 4.34% of that of the acrylic acid fed to the reactor.

EXAMPLE 2

In the same apparatus as used in Example 1, the reactor was first charged with 14 liters of a strongly acidic cation-exchange resin (produced by Mitsubishi Chemical Industries, Ltd. and marketed under trademark designation of "Diaion PK-208") and then supplied with a mixed solution comprising 49.0% of acrylic acid, 36.6% of 2-ethylhexanol, 14.2% of 2-ethylhexyl acrylate, and 0.1% of water until the amount of the contents of the reactor reached 50 liters. The revolution number of the stirrer was adjusted so that the motive force of stirring would reach 0.05 kW per m³ of the reaction solution and the amount of steam supplied to the heating jacket of the reactor would reach 85° C. and the pressure within the reactor was adjusted to 70 mmHg (absolute). Through the raw material feeding pipe, a mixed solution comprising 49.0% of acrylic acid, 36.6% of 2-ethylhexanol, 14.2% of 2-ethylhexyl acrylate, and 0.1% of water was fed in at a rate of 23.5 kg per hour. Through the top of the distillation tower, 2-ethylhexanol as supplied at a rate of 13.2 kg per hour. To prevent polymerization in the distillation tower and the reactor, phenothiazine was fed into the distillation tower through the top thereof at a rate of 0.05% based on the amount of the acrylic acid supplied. The reaction was continued, with the reaction solution partly withdrawn through the bottom of the reactor so as to keep the total amount of the contents of the reactor at the fixed level of 50 liters, until the interior of the reactor was stabilized. While the interior of the reactor was in the stabilized state, the organic phase was distilled out through the top of the distillation tower at a rate of 0.18 kg/hr and the water phase at a rate of 1.69 kg/hr and the reaction solution was withdrawn through the bottom of the reactor at a rate of 34.83 kg/hr. The reaction solution withdrawn via the bottom of the reactor contained 13.41% of acrylic acid, 26.56% of 2-ethylhexanol, 59.47% of 2-ethylhexyl acrylate, 0.11% of water, 0.06% of dimeric acid, 0.13% of 2-ethylhexyl ester of dimer acid, and 0.03% of 2-ethylhexyl hydropropionate. The organic phase distilled out through the top of the distillation tower was a 2-ethylhexanol phase containing 0.003% of acrylic acid, 3.70% of iso-octene, and 2.50% of water. The water phase similarly distilled contained 0.002% of acrylic acid and 0.08% of 2-ethylhexanol. These results of reaction indicate that the conversion of acrylic acid was 59.5% and that of 2-ethylhexanol was 56.8% and the selectivity and 2-ethylhexyl acrylate was 99.20 mol% based on acrylic acid and 99.12 mol% based on 2-ethylhexanol. The acrylic acid distilled out through the top of the distillation tower was in a barely detectable amount.

Control 1

A reaction was carried out by the use of a reactor of stainless steel 500 mm in inside diameter provided on the outer side thereof with a heating jacket, in the bottom part thereof of a raw material feeding pipe, and in the upper part thereof with a reaction solution discharge pipe and a distillation tower 100 mm in inside diameter. The distillation tower was packed with metal gauze made of stainless steel as packings and the raw material feeding pipe and the reaction solution discharge pipe were both fitted with a metal gauze of 80 mesh.

The reactor was first packed in the form of fixed bed with 81 liters (on dry basis) of a strongly acidic cation-exchange resin (produced by Mitsubishi Chemical Industries, Ltd. and marketed under trademark designation of "Diaion PK-208") and then supplied through the raw material feeding pipe with a mixed solution comprising 31.6% of acrylic acid, 61.5% of 2-ethylhexanol, 6.6% of 2-ethylhexyl acrylate, and 0.3% of water at a feed rate of 60.0 kg per hour. To prevent polymerization in the distillation tower and the reactor, phenothiazine was fed into the distillation tower through the top thereof at a rate of 0.05% based on the amount of the acrylic acid supplied. The amount of steam supplied to the heating jacket of the reactor was adjusted so that the temperature of the reaction solution would reach 85° C. and the pressure in the reactor was adjusted to 70 mmHg (absolute). Under these conditions, the reaction was continued until the interior of the system was stabilized. While the interior of the system was in the stabilized state, the organic phase was distilled out through the top of the distillation tower at a rate of 0.61 kg per hour and the water phase at a rate of 3.36 kg per hour and the reaction solution was withdrawn through the top of the reactor at a rate of 56.03 kg per hour. The reaction solution withdrawn through the top of the reactor contained 11.55% of acrylic acid, 28.29% of 2-ethylhexanol, 57.31% of 2-ethylhexyl acrylate, 0.41% of water, 0.28% of dimer acid, 1.16% of 2-ethylhexyl ester of dimeric acid, and 0.54% of 2-ethylhexyl hydroxypropionate. The organic phase distilled out through the top of the distillation tower contained 29.5% of acrylic acid, 9.84% of iso-octene, 6.56% of water, and the balance of 2-ethylhexanol. The water phase similarly distilled contained 19.6% of acrylic acid and 0.30% of 2-ethylhexanol. These results of reaction indicate that the conversion of acrylic acid was 61.5% and that of 2-ethylhexanol was 56.1% and the selectivity of 2-ethylhexyl acrylate was 94.28 mol% based on acrylic acid and 96.14 mol% based on 2-ethylhexanol. The amount of the acrylic acid distilled out through the top of the distillation tower was 4.43% of that of the acrylic acid supplied to the reactor.

Control 2

A reaction was carried out by using a reactor of stainless steel 500 mm in inside diameter provided on the outer side thereof with a heating jacket, in the bottom part thereof with a raw material feeding pipe, and in the upper part thereof with a reaction solution discharge pipe and a distillation tower 100 mm in diameter.

The distillation tower was packed with metal gauze made of stainless steel as packings. The raw material feeding pipe, and the reaction solution discharge pipe were each fitted with a metal gauze of 80 mesh.

The reactor was first packed in the form of fixed bed with 81 liters (on dry basis) of a strongly acidic cation-exchange resin (produced by Mitsubishi Chemical Industries, Ltd. and marketed under trademark designation of "Diaion PK-208.) and then supplied via the raw material feeding pipe in the bottom part with a mixed solution comprising 49.2% of acrylic acid, 40.1% of 2-ethylhexanol, 10.3% of 2-ethylhexyl acrylate, and 0.3% of water at a flow rate of 38.55 kg per hour and via the top of the distillation tower with 2-ethylhexanol at a flow rate of 21.4 kg per hour. To prevent polymerization in the distillation tower and the reactor, phenothiazine was fed into the distillation tower through the top thereof at a rate of 0.05% based on the amount of acrylic acid supplied. The amount of steam supplied to the heating jacket of the reactor was adjusted so that the temperature of the reaction solution would reach 85° C. and the pressure in the reactor was adjusted to 70 mmHg (absolute).

While the interior of the system was in a stabilized state, the organic phase was distilled out through the top of the distillation tower at a rate of 0.3 kg per hour and the water phase was similarly distilled out at a rate of 2.71 kg per hour and the reaction solution was withdrawn through the top of the reactor at a rate of 56.94 kg per hour. The reaction solution withdrawn through the top of the reactor contained 12.56% of acrylic acid, 27.34% of 2-ethylhexanol, 57.04% of 2-ethylhexyl acrylate, 0.40% of water, 0.28% of dimer acid, 1.16% of 2-ethylhexyl ester of dimeric acid, and 0.54% of 2-ethylhexyl hydroxypropionate. The organic phase distilled out through the top of the distillation tower was a 2-ethylhexanol phase containing 4.33% of iso-octene and 2.47% of water. The water phase contained 0.002% of acrylic acid and 0.08% of 2-ethylhexanol.

These results of reaction indicate that the conversion of acrylic acid was 62.3% and the conversion of 2-ethylhexanol was 57.0% and the selectivity of 2-ethylhexyl acrylate was 94.18 mol% based on acrylic acid and 95.93 mol% based on 2-ethylhexanol.

Industrial Applicability

The present invention, in the esterification of (meth)acrylic acid and an aliphatic alcohol of 1 to 12 carbon atoms in the presence of a strongly acidic cation-exchange resin, notably represses otherwise conspicuous secondary reactions and permits the corresponding ester to be produced in a high yield by keeping the reaction solution in a boiling state and using the catalyst in a state fluidized with a stirrer adapted to generate desired stirring with a motive force falling in a specific range.

Since the method of this invention effects the esterification with the reaction solution kept in the boiling state, when aliphatic alcohol to be used therein has 1 to 4 carbon atoms, the esterification can be carried out in a continuous mode by providing the reactor with a distillation tower thereby permitting separation of the produced ester and the formed water by virtue of distillation. When the aliphatic alcohol to be used has 4 to 12 carbon atoms, the occurrence of such as iso-octene can be repressed and the corresponding ester can be produced in a high yield by providing the reactor with a distillation tower and refluxing the alcohol as raw material into the distillation tower through the top thereof thereby enabling the formed water to be separated by distillation.

Any of the embodiments of the present invention offers a great advantage that the amount of the catalyst to be used effectively therein is notably small and, consequently, the apparatus for the esterification is quite compact as compared with the method using the catalyst in the form of a fixed bed.

What is claimed is:

1. A method for the production of a corresponding ester by the reaction of acrylic acid or methacrylic acid with an aliphatic alcohol of 1 to 12 carbon atoms in the presence of a strongly acidic cation-exchange resin as a catalyst, which method is characterized by keeping the reaction solution in a boiling state and keeping said catalyst suspended and dispersed in the reaction solution with a stirrer operated with a motive force in the range of 0.005 to 2 kW per $m^3$ of the reaction solution.

2. A method according to claim 1, wherein the molar ratio of acrylic acid or methacrylic acid to said aliphatic alcohol is in the range of 1:0.5 to 1:3, the reaction temperature in the range of 50° to 150° C., and the reaction pressure (absolute) in the range of 20 to 760 mmHg.

3. A method according to claim 1, wherein the amount of said strongly acidic cation-exchange resin to be used is in the range of 10 to 60% by volume based on the total amount of said reaction solution and said resin.

4. A method according to claim 1, wherein said strongly acidic cation-exchange resin possesses a particle diameter in the range of 0.1 to 2.0 mm, a cross-linking degree in the range of 2 to 20%, a specific surface area in the range of 0.1 to 5 $m^2/g$, and a porosity of not more than 10% by volume.

5. A method according to claim 1, wherein said aliphatic alcohol is 2-ethylhexanol.

6. A method for the production of a corresponding ester by the reaction of acrylic acid or methacrylic acid with an aliphatic alcohol of 4 to 12 carbon atoms in the presence of a strongly acidic cation-exchange resin as a catalyst, which method is characterized by keeping the reaction solution in a boiling state and keeping said catalyst suspended and dispersed in the reaction solution with a stirrer operated with a motive force in the range of 0.005 to 2 kW per $m^3$ of the reaction solution, refluxing the same alcohol into contact with the vapor distilled out of the esterification system and composed mainly of the water formed by esterification thereby separating the acrylic acid or methacrylic acid entrained by said formed water from the formed water, and recovering the separated acid.

7. A method according to claim 6, wherein said aliphatic alcohol possesses 5 to 12 carbon atoms.

8. A method according to claim 6, wherein the molar ratio of acrylic acid or methacrylic acid to said aliphatic alcohol is in the range of 1:0.5 to 1:3, the reaction temperature in the range of 50° to 150° C., and the reaction pressure (absolute) in the range of 20 to 760 mmHg.

9. A method according to claim 6, wherein the amount of said strongly acidic cation-exchange resin to be used is in the range of 10 to 60% by volume based on the total amount of said reaction solution and said resin.

10. A method according to claim 6, wherein said strongly acidic cation-exchange resin possesses a particle diameter in the range of 0.1 to 2.0 mm, a cross-linking degree in the range of 2 to 20%, a specific surface area in the range of 0.1 to 5 $m^2/g$, and a porosity of not more than 10% by volume.

11. A method according to claim 6, wherein the amount of said alcohol supplied for reflux is at least 10% by weight of the amount of said alcohol supplied for said esterification.

12. A method according to claim 6, wherein said aliphatic alcohol is 2-ethylhexanol.

* * * * *